US011944380B1

(12) United States Patent
Kellner et al.

(10) Patent No.: US 11,944,380 B1
(45) Date of Patent: Apr. 2, 2024

(54) SYSTEMS AND METHODS TO FACILITATE VISION SCREENING AND REPORTING

(71) Applicant: Welch Allyn, Inc., Skaneateles Falls, NY (US)

(72) Inventors: David L. Kellner, Baldwinsville, NY (US); Jennifer Bergstrom, Portland, OR (US); Eric J. Laurin, Beaverton, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 816 days.

(21) Appl. No.: 17/028,996

(22) Filed: Sep. 22, 2020

Related U.S. Application Data

(60) Provisional application No. 62/905,986, filed on Sep. 25, 2019.

(51) Int. Cl.
| A61B 3/028 | (2006.01) |
| A61B 3/11 | (2006.01) |
| A61B 3/113 | (2006.01) |
| A61B 5/00 | (2006.01) |
| A61B 5/117 | (2016.01) |

(Continued)

(52) U.S. Cl.
CPC ............ *A61B 3/028* (2013.01); *A61B 3/111* (2013.01); *A61B 3/112* (2013.01); *A61B 3/113* (2013.01); *A61B 5/0013* (2013.01); *A61B 5/0022* (2013.01); *A61B 5/117* (2013.01); *A61B 5/74* (2013.01); *G16H 10/60* (2018.01); *G16H 20/00* (2018.01)

(58) Field of Classification Search
CPC ......... A61B 3/028; A61B 3/111; A61B 3/112; A61B 3/113; A61B 5/0013; A61B 5/0022; A61B 5/117; A61B 5/74; G16H 10/60; G16H 20/00
USPC .......................................................... 351/206
See application file for complete search history.

(56) References Cited

U.S. PATENT DOCUMENTS

| 6,003,991 A | 12/1999 | Viirre |
| 9,743,828 B2 | 8/2017 | Bartlett et al. |
| 2004/0110119 A1 | 6/2004 | Riconda et al. |

(Continued)

FOREIGN PATENT DOCUMENTS

| CN | 202044244 U | 11/2011 |
| CN | 202044245 U | 11/2011 |

(Continued)

*Primary Examiner* — Mohammed A Hasan
(74) *Attorney, Agent, or Firm* — Lee & Hayes, P.C.

(57) ABSTRACT

Various implementations disclosed herein relate to systems, methods, and devices to facilitate mass vision screening of individuals. An example method includes capturing a first image of an individual and confirming an identity of the individual based on the first image. In response to confirming the identity of the individual, the method may further include capturing one or more second images of an eye of the individual; determining one or more health metrics of the individual based on the one or more second images, and transmitting, to a remote device, the identity of the individual and the one or more health metrics of the individual. The one or more health metrics may include at least one of a pupillary distance of the individual, a pupil size of the eye of the individual, a complete refraction of the eye of the individual, or an alignment indicator of the eye of the individual.

19 Claims, 8 Drawing Sheets

(51) Int. Cl.
*G16H 10/60* (2018.01)
*G16H 20/00* (2018.01)

(56) References Cited

U.S. PATENT DOCUMENTS

| | | | | |
|---|---|---|---|---|
| 2014/0055589 | A1* | 2/2014 | Bangera | A61B 5/4848 |
| | | | | 348/E7.085 |
| 2017/0323056 | A1* | 11/2017 | Govro | G16H 10/60 |
| 2018/0115527 | A1* | 4/2018 | Armitage | H04L 63/0421 |
| 2018/0218643 | A1* | 8/2018 | Wexler | G09B 21/006 |
| 2018/0233219 | A1* | 8/2018 | Cathcart | G06Q 40/08 |
| 2020/0126660 | A1* | 4/2020 | Costantino | G16H 10/65 |

FOREIGN PATENT DOCUMENTS

| | | |
|---|---|---|
| CN | 105105705 A | 12/2015 |
| CN | 106175658 A | 12/2016 |
| JP | 2000262469 A | 9/2000 |
| WO | WO2006047369 A2 | 5/2006 |
| WO | WO2015176573 A1 | 11/2015 |

* cited by examiner

SYSTEMS AND METHODS TO FACILITATE VISION SCREENING AND REPORTING

CROSS-REFERENCE TO RELATED APPLICATION

The present application claims the priority of U.S. Provisional Application No. 62/905,986, which was filed on Sep. 25, 2019 and is incorporated by reference herein in its entirety.

FIELD OF THE INVENTION

The present application relates to systems and methods for performing automated vision screening on individuals, such as children in a school environment. In addition, the present application relates to systems and methods for tracking the results of vision screening examinations outside of a healthcare environment, such as by teachers in a classroom environment.

BACKGROUND

By performing regular eye examinations and vision assessments on children, care providers can detect various conditions that result in vision impairment, indicate serious disease, lead to problems with school performance, or the like. As of 2019, the American Academy of Pediatrics (AAP) recommends yearly vision screening for school-age children between the ages of 5 and 18 years.

A care provider performing an eye examination on a patient can evaluate various features relating to vision and eye physiology. For instance, the care provider can assess the patient's visual system, as well as determine the presence of retinal abnormalities, cataracts, glaucoma, retinoblastoma, strabismus, or the like. In addition, the care provider may be able to determine whether the patient is potentially suffering from various neurologic disorders, such as amblyopia, during the eye examination. In some cases, the care provider can identify a refractive error of the patient.

Optometrists, ophthalmologists, and other care providers must undergo rigorous training to be able to perform thorough eye examinations on patients. Many individuals can lack the resources to seek specialists for eye examinations. School districts often provide subsidized, low- to no-cost vision screening for students to ensure that eye-related health problems are assessed and diagnosed early in various students, regardless of socioeconomic status. Vision screening can be performed on a large number of individuals (e.g., students) by untrained volunteers operating specialized equipment. When an operator identifies an abnormality in a patient through vision screening, the operator can refer the patient to a specialist for a full eye examination.

SUMMARY

Mass vision screening of students can be difficult in a variety of ways. For instance, operators performing mass vision screening may be unable to confirm the identities of the students being screened. Accordingly, results of the vision screening may be associated with the wrong student identities.

In some implementations, various systems and methods can be used to automatically confirm the identities of the students. In various examples, students may wear personalized stickers during a vision screening event. Each sticker, for example, may display a barcode associated with an identity of the student wearing the sticker. In some cases, a camera used to perform the vision screening may also capture images of the barcodes displayed on the stickers. Using the captured images of the barcodes, a computer system can confirm the identities of the students. In some cases, multiple stickers can be automatically generated based on an electronic list of students to be screened during the vision screening event.

In some cases, the identities of the students can be confirmed based on image recognition. For instance, the camera may capture images of faces of the students. The computer system can confirm the identities of the students by comparing the images to previously obtained images of the faces.

The camera may additionally perform vision screening on the students. Because the identities of the students have been separately confirmed, the results of the vision screening can be accurately associated with the appropriate student identities.

In some cases, the results can be output to an operator via an electronic device during the vision screening event. The results can be stored in association with the appropriate student identities in an electronic database, such as a health record database. According to various examples, the results associated with a given student may be used to assess whether the student should be referred to an eye care specialist for further analysis. In some cases, the results may be stored in an educational profile associated with the given student. The educational profile may be accessible by a teacher of the student. Accordingly, if the student is experiencing difficulty in school, the teacher can identify whether vision problems may be a contributing factor of that difficulty.

DESCRIPTION OF THE FIGURES

The following figures, which form a part of this disclosure, are illustrative of described technology and are not meant to limit the scope of the claims in any manner.

DETAILED DESCRIPTION

Figure 1:
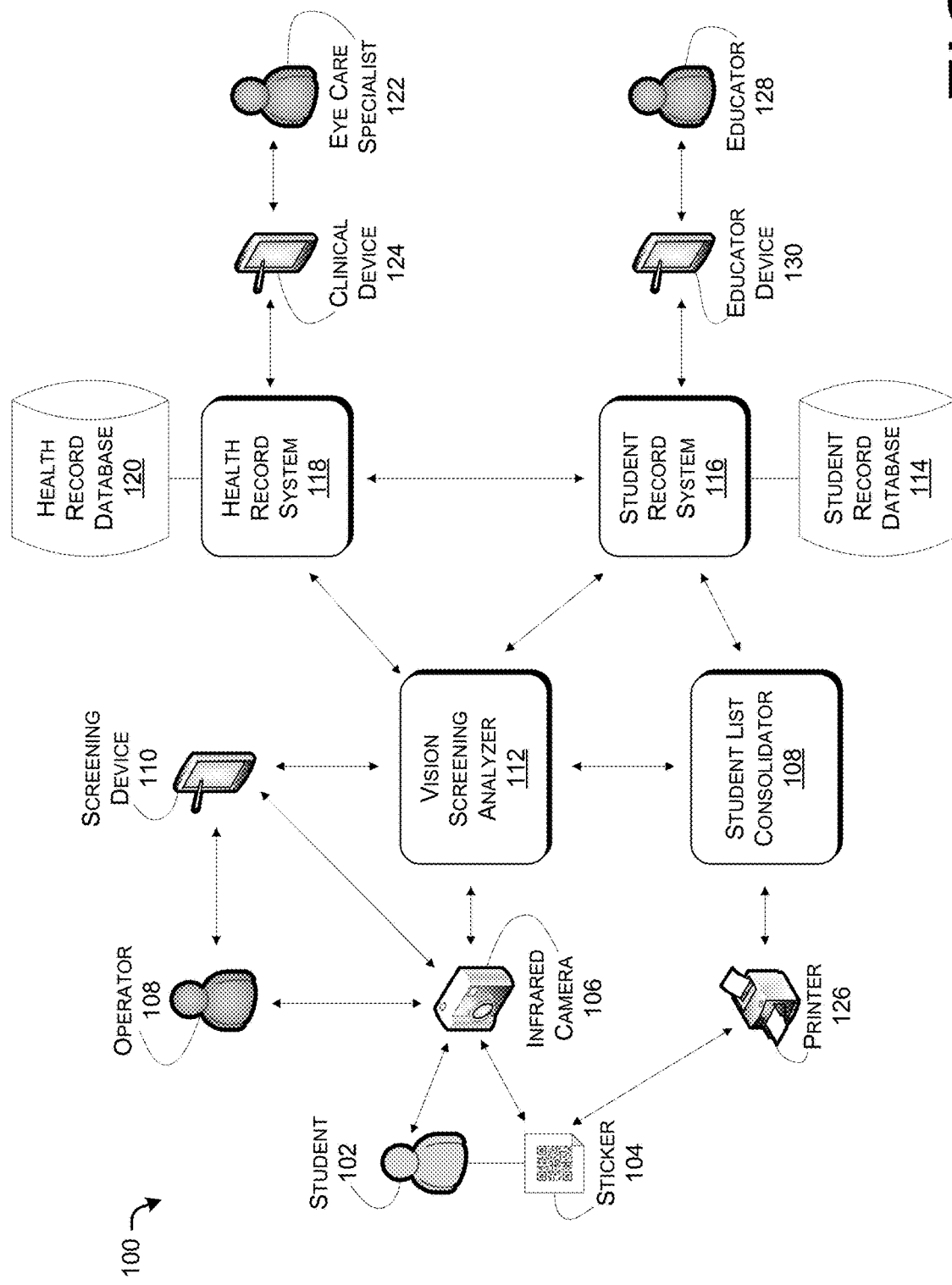
FIG. 1 illustrates an example environment for vision screening and reporting.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

FIG. 1 illustrates an example environment 100 for vision screening and reporting. As illustrated, the environment 100 can be used to assess the eye-related health metrics of a student 102. In some cases, the environment 100 may be used to perform mass vision screening of multiple students including the student 102. In various implementations, the student 102 may be enrolled in a school. The student 102 may have an age of 5 to 18, in some cases.

The student 102 may be wearing a sticker 104 that can be used to indicate the identity of the student 102. In various implementations, a barcode may be printed on the sticker 104, and the barcode may indicate the identity of the student. As used herein, the term "barcode" may refer to any visual, machine-readable representation of data. A barcode can be 1-Dimensional (1D) (e.g., a code similar to a Universal Product Code (UPC), an International Standard Book Number (ISBN), or the like), 2-Dimensional (2D) (e.g., a Quick Response (QR) code, a High Capacity Color Barcode (HCCB), or the like), or may have greater than two dimensions. In some cases, the barcode may be represented by two colors (e.g., a QR code) or by greater than two colors (e.g., an HCCB).

In various implementations, the barcode on the sticker 104 may encode a student code. As used herein, the term "student code" may refer to a code that uniquely identifies an individual student (e.g., the student 102) among multiple students being screened in a vision screening event. In some examples, the student code of the student 102 may include at least one of a number associated with the student 102, a string of alphanumeric characters representing the student 102, a name (e.g., a first and last name) of the student 102, a date-of-birth of the student 102, a gender of the student 102, an age of the student 102, an identifier (e.g., a name) of a teacher of the student 102, or the like.

In some cases, the barcode may encode a Uniform Resource Locator (URL) identifying a website associated with the student 102. For instance, the website may display health and/or educational records of the student 102. In some example implementations, the website may be updated based on vision screening results of the student 102. The website may display a user interface that reports the results of the vision screening results. For instance, a parent of the student 102 may scan the barcode of the student 102 using a camera (e.g., a camera in a smart phone) and access the website. Using the website, the parent may identify a status of the vision of the student 102 (e.g., whether the student may need glasses), whether the student 102 should have a follow-up appointment with a specialist, or the like.

As used herein, the term "sticker" may refer to an object including a substrate having at least one side is at least partially coated with an adhesive. In various implementations of the present disclosure, the sticker 104 may include a substrate having a first side and a second side, wherein the first side is at least partially coated with an adhesive and the second side is printed with ink representing the barcode. The substrate may include at least one of paper, plastic, vinyl, or some other solid and/or flexible material. The adhesive may include a pressure-sensitive adhesive, such as at least one of an acrylic composition, an acrylate composition, butyl rubber composition, an ethylene-vinyl acetate (EVA) composition, a natural rubber composition, a nitrile composition, a silicone rubber composition, a silicate resin composition, a trimethyl silane composition, a Styrene Block Copolymer (SBC) composition, a Styrene-Butadiene-Styrene (SBS) composition, a Styrene-Ethyl/Butylene-Styrene (SEBS) composition, a Styrene-Ethylene/Propylene (SEP) composition, a Styrene-Isoprene-Styrene (SIS) composition, a vinyl ether composition, or the like. The ink may include an ink suitable for inkjet printing. In some cases, the ink can include at least one of a solvent ink, an Ultraviolet (UV)-curable ink, a dye sublimation ink, a hot melt ink, or the like. In various examples, the ink may be a non-toxic ink suitable for manipulation by children. According to some implementations, the ink may be visible in an infrared spectrum (e.g., with a stimulation wavelength and/or emission wavelength that is in a range of 700 to 900 nanometers). In some cases, to enhance security and/or privacy of the student 102, the ink may not be visible in a visible light spectrum. Thus, in some examples, the barcode printed on the sticker 104 may be invisible to the human eye, but can be imaged by a camera configured to capture infrared images.

An infrared camera 106 may be configured to capture at least one image of the student 102, the sticker 104, or a combination thereof. According to some implementations, the image(s) can be captured by a barcode reader, a barcode scanner, a visible light camera, or the like associated with the infrared camera 106. In some cases, the infrared camera 106 (and/or the visible light camera, or the like) may capture at least one infrared and/or visible light image of a face of the student 102. The infrared camera 106 (and/or the barcode reader, the barcode scanner, the visible light camera, or the like) may capture at least one infrared and/or visible light image of the barcode on the sticker 104. The image(s) of the face of the student 102 and/or the barcode on the sticker 104 may be used to confirm the identity of the student 102. In various implementations, the infrared camera 106 may also be configured to capture one or more images of eyes of the student 102. The images of the eyes can be used to assess eye-related health metrics of the student 102. In various examples, the infrared camera 106 can capture 1D images, 2D images, three-dimensional (3D) images, video, or the like. In some cases, the infrared camera 106 can include a barcode scanner or reader configured to generate an image of a barcode. In various examples, the infrared camera 106 can include a visible light camera configured to capture visible light images.

The infrared camera 106 may be configured to capture one or more images of the eyes of the student 102. For instance, the infrared camera 106 may emit a flash onto an eye of the student 102 and capture a digital image of a resultant red reflex of the eye. In some cases, the infrared camera 106 may capture images of the red reflexes of both eyes of the student 102. According to various examples, the infrared camera 106 may be configured to emit infrared radiation, to direct the infrared radiation onto an eye of the student 102, and to capture a digital image of a reflection of the infrared radiation. This captured image may be used to perform autorefraction or other analysis. In some cases, the infrared camera 106 may include an output device configured to output images, light, and/or sound to attract the attention of the student 102 during a vision screening process.

The infrared camera 106 may be operated by an operator 108. The operator 108 may input a presumed identity of the student 102 into an input device of the screening device 110. For example, the operator 108 may ask the student 102 for his or her name and type the name into the screening device 110. The infrared camera 106 and/or the screening device 110 may output a non-technical user interface through which the operator 108 can operate the infrared camera 106.

In various examples, the screening device 110 is configured to perform, and/or enable the operator 108 to perform, vision screening of the student 102. Accordingly, in various examples, the operator 108 need not be an eye care specialist to perform vision screening of the student 102 using the infrared camera 106 and/or the screening device 110. In some implementations, the operator 108 may verify the identity of the student 102 by comparing an image of a student to be screened, which may be output (e.g., displayed) by the screening device 110, to the operator's 108 direct view of the student 102 during the screening event. In some instances, the infrared camera 106 and the screening device 110 may be incorporated into a single system or device, such as a SPOT™ Vision Screener. In particular, although the infrared camera 106 and the screening device 110 are schematically illustrated in FIG. 1 as comprising separate devices, in some examples, the infrared camera 106 may comprise a component of the screening device 110 or vice versa.

In some cases, the screening device 110 may be configured to perform, and/or enable the operator 108 to perform, other types of screening. For example, the screening device 110 may include an eye mobility testing device configured to determine how well the two eyes of the student 102 move together while tracking an image. For example, the eye mobility testing device may show text to the student 102 and record a video of the eyes of the student 102 as the student is reading the displayed text. In some cases, the fixation and/or saccadic events can be identified by the screening device 110 based on the video. The eye mobility testing device may be utilized in a concussions screening of the student 102. In some cases, the eye mobility testing device can be used to determine whether the student 102 has developmental or other issues associated with eye mobility, which may show that vision therapy or a neurological assessment is indicated for the student 102. For example, the fixation and/or saccadic events may indicate that the student 102 has dyslexia.

The screening device 110 can be a User Equipment (UE) connected to the infrared camera 106 via one or more wired and/or wireless communication interfaces. As used herein, the terms "UE," "user device," "wireless communication device," "communication device," "mobile device," "client device," and "terminal" can be used interchangeably herein to describe any UE that is capable of transmitting/receiving data (e.g., wirelessly) using any suitable communications/data technology, protocol, or standard, such as Global System for Mobile Communications (GSM), Time Division Multiple Access (TDMA), Universal Mobile Telecommunications System (UMTS), Evolution-Data Optimized (EVDO), Long Term Evolution (LTE), Advanced LTE (LTE+), New Radio (NR), Generic Access Network (GAN), Unlicensed Mobile Access (UMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), High Speed Packet Access (HSPA), evolved HSPA (HSPA+), Voice over Internet Protocol (IP) (VoIP), VoLTE, Institute of Electrical and Electronics Engineers' (IEEE) 802.1x protocols, WiMAX, Wi-Fi, Data Over Cable Service Interface Specification (DOCSIS), digital subscriber line (DSL), and/or any future IP-based network technology or evolution of an existing IP-based network technology. In general, a UE can be implemented as any suitable type of computing device configured to communicate over a wired or wireless network, including, without limitation, a mobile phone (e.g., a smart phone), a tablet computer, a laptop computer, a Portable Digital Assistant (PDA), a wearable computer (e.g., electronic/smart glasses, a smart watch, fitness trackers, etc.), an Internet-of-Things (IoT) device, an in-vehicle (e.g., in-car) computer, and/or any similar mobile device, as well as situated computing devices including, without limitation, a television (smart television), a Set-Top-Box (STB), a desktop computer, and the like.

The infrared camera 106 may be configured to transmit images of the student 102 and/or the sticker 104 to a vision screening analyzer 112. In various implementations, at least one of the infrared camera 106, the screening device 110, or the vision screening analyzer 112 may be referred to as a "vision screener." For instance, the infrared camera 106 may package the images into data packets and transmit the data packets to the vision screening analyzer 112 over one or more communication interfaces. In various implementations, the vision screening analyzer 112 may be configured to confirm an identity of the student 102 based on at least some of the images. As used herein, an "identity" of an individual may refer to at least one of a name of the individual, an age of the individual, a date of birth of the individual, a name of a teacher of the individual, a gender of the individual, or an identification (ID) number of the individual.

According to some examples, the vision screening analyzer 112 may extract a student code encoded into the barcode depicted in an image of the sticker 104. In some cases, the vision screening analyzer 112 may access a database storing entries associated with various students including the student 102. The entries may be indexed according to student code. The vision screening analyzer 112 may identify the entry associated with the student 102 based on the extracted student code. The entry may include a profile identifying the student 102. For example, the profile may include at least one of a name of the student 102, an age of the student 102, a date of birth of the student 102, a name of a teacher of the student 102, a gender of the student 102, or an identification number of the student 102. Accordingly, the vision screening analyzer 112 may identify an identity of the student 102 based on the barcode.

In some instances, the vision screening analyzer 112 may perform facial recognition on an image of the student 102. In some cases, the vision screening analyzer 112 may receive a first image of a face of the student 102 captured by the infrared camera 106 or another type of camera (not illustrated), such as a digital camera configured to capture visible light images of the face of the student 102. The vision screening analyzer 112 may identify a second image of the face of the student 102 that has been previously captured. In some cases, the second image is stored locally on the vision screening analyzer 112 and associated with an identity of the student 102. In some instances, the vision screening analyzer 112 receives the second image from a student record database 114 associated with a student record system 116. For example, the second image may be associated with a student profile in a record of the student 102. The vision screening analyzer 112 may confirm the identity of the student 102 by comparing the first image and the second image. In some examples, the vision screening analyzer 112 may apply a facial recognition technique to compare the first image and the second image, such as a technique utilizing principal component analysis using Eigenfaces, linear discriminant analysis, elastic bunch graph matching using the Fisherface algorithm, hidden Markov models, multilinear subspace learning using tensor representation, or the like. In some cases, the vision screening analyzer 112 may identify the student 102 based on one or more images of the eyes of the student 102. For example, the vision screening analyzer 121 can capture an image of a visual pattern of an iris of the student 102 and compare the image to a pre-stored image of the iris of the student 102. In some cases, the vision screening analyzer 121 can identify the student 102 based on retinal recognition techniques. Accordingly, the vision screening analyzer may identify the identity of the student 102 based on facial recognition.

In various examples, the vision screening analyzer 112 may identify the identity of the student 102 based on an input received by the screening device 110 from the operator 108. For instance, the operator 108 may input a string identifying the student 102 into the screening device 110. The screening device 110 may transmit an indication of the input to the vision screening analyzer 112, and the vision screening analyzer 112 may identify the identity of the student 102.

In some cases, the students (including the student 102) may be screened in a predetermined order. A list of the identities of the students may be provided to the vision screening analyzer 112. For instance, the student record system 116 may transmit the list of identities to the vision screening analyzer 112. In some cases, the vision screening analyzer 112 may store the list of the identities. Accordingly, the vision screening analyzer may determine the identity of the student 102 based on the list and the arrangement of the student 102 among the students in the vision screening process.

According to various implementations, the vision screening analyzer 112 may confirm the identity of the student 102 based on two or more methods of identifying the identity of the student 102. For example, the vision screening analyzer 112 may determine the identity of the student 102 via the barcode on the sticker 104 and may confirm the identity of the student 102 based on facial recognition. Accordingly, the accuracy by which vision screening results of the student 102 can be associated with the identity of the student 102 can be enhanced.

In some cases, the vision screening analyzer 112 may output a name and/or pre-stored image of whatever student is associated with the barcode depicted by the sticker 104. For example, the name and/or pre-stored image can be extracted, based on the barcode, from the student record database 114. The operator 108, who may be familiar with the student 102, can review the name and/or pre-stored image in order to confirm that the student 102 is associated with the correct sticker 104 prior to screening the student 102.

The vision screening analyzer 112 may also determine one or more health metrics of the student 102 based on images of the eyes of the student 102. For instance, the vision screening analyzer 112 may analyze the red reflex of each eye of the student 102 to determine if there are dark spots (e.g., any heterogeneous color distribution, presence of a non-red spot, etc.) in either red reflex, asymmetry between the red reflexes, and/or the presence of a white reflex in either eye.

In some examples, the vision screening analyzer 112 may perform autorefraction on the student 102 by analyzing an image of infrared light reflected from the eye of the student 102 to identify a size and/or shape of the infrared light reflected from a retina of the eye. In various implementations, the vision screening analyzer 112 may automatically perform eccentric photorefraction on the student 102, in order to identify at least one refractive error, at least one squint, and/or at least one media opacity of the student 102. For instance, the vision screening analyzer 112 may cause a light to shine on a pupil of the student 102, the infrared camera 106 may capture an image of the pupil illuminated by the light, and the vision screening analyzer 112 may identify a crescent of light in the pupil depicted in the image. The vision screening analyzer 112 may estimate the refractive error of the student 102 based on the width (e.g., the extent of the crescent along the pupil meridian) of the crescent of light. The size of the crescent can correspond to defocus of the eye of the student 102 with respect to position of the infrared camera 106. In addition, the vision screening analyzer 112 may analyze an intensity distribution across the vertical meridian of the pupil depicted in the image. The intensity distribution may correspond to the refractive state of the eye of the student 102.

In some cases, the vision screening analyzer 112 may control the infrared camera 106 to capture multiple images of the reflection of infrared light at different magnification levels, and identify a particular magnification level at which the size and/or shape of the reflected infrared light indicates the eye is in focus. Based on the particular magnification level, a refractive error (e.g., refraction, sphere, cylinder, axis, etc.) of the eye of the student 102 can be identified by the vision screening analyzer 112.

The health metric(s) of the student 102 can be identified by analyzing the red reflex and/or the refractive error of one or both eyes of the student 102. As used herein, the term "health metric" can refer to at least one of the presence or absence of dark spots in a red reflex, the presence or absence of asymmetry between eyes, an alignment of eyes, the presence or absence of a white reflex, a refractive error of an eye, a pupillary distance of eyes, a pupil size of an eye, a complete refraction of an eye, a message indicating an individual should follow up with an eye care specialist for an eye exam, an eye movement event (e.g., fixation and/or saccadic events) indicative of a concussion and/or potential neurological condition, any result of an eye exam, any result of a vision screening, or the like.

In various implementations, the vision screening analyzer 112 may transmit a message indicating the health metric(s) of the student 102 to a health record system 118. In some cases, the message may also indicate the identity of the student 102, which may have been confirmed by the vision screening analyzer 112 via two or more identification methods. The health record system 118 may store the health metric(s) of the student 102 in a health record associated with the student 102. The health record may be stored in a health record database 120. The health record database 120 may be an electronic database, in various implementations.

In some cases, the vision screening analyzer 112 may identify whether the student 102 should be further assessed eye care specialist 122. The eye care specialist 122 may be a physician, optometrist, ophthalmologist, or any other individual with specialized training that can perform a full eye exam on the student 102. The vision screening analyzer 112 may determine that the student 102 should follow up with the eye care specialist 122 when the vision screening analyzer 112 determines that one or more of the health metric(s) are abnormal. For instance, the vision screening analyzer 112 may determine that the student 102 should be assessed by the eye care specialist 122 in response to identifying at least one of the presence of dark spots (e.g., any color heterogeneity) on at least one red reflex of the student 102, that a greater than threshold level of asymmetry exists between the red reflexes of the eyes of the student 102, the presence of a white reflex in the eyes of the student 102, that the refractive error is above a particular threshold, or the like. In various implementations, the vision screening analyzer may transmit a message indicating that the student 102 should follow up with the eye care specialist 122 to the health record system 118. In some cases, the health record system 118 may automatically schedule a follow-up appointment for the student 102 with the eye care specialist 122. The health record system 118 may store, in the health profile of the student 102, an indication that the student 102 should follow up with the eye care specialist 122.

In various implementations, the health record system 118 may host and/or manage the website and/or URL linked to the barcode of the sticker 104. The health record system 118 may update the website based on the results of the vision screening. For instance, the health record system 118 may cause the website to display one or more of the health metric(s) of the student. In some examples, the health record system 118 may update the website with an indication of whether the student 102 should follow up with the eye care specialist 122. Accordingly, someone (e.g., a parent) scanning the barcode of the sticker 104 after the vision screening takes place could efficiently identify the results of the vision screening. In addition, in some cases, the sticker 104 may provide a more reliable method of reporting the results of the vision screening than requiring the student 102 to self-report the results of the vision screening to a parent or guardian.

The health record system 118 may be in communication with a clinical device 124 associated with the eye care specialist 122. In some implementations, the health record system 118 may transmit the health metric(s) identified by the vision screening analyzer 112 to the clinical device 124. The clinical device 124 may output the health metric(s) to the eye care specialist 122. Accordingly, the eye care specialist 122 may be informed of the results of the vision screening during a follow-up eye exam with the student 102.

In various implementations, the environment 100 may also be used to generate the sticker 104. In some examples, the student list consolidator 108 may receive a student list from the student record system 116. The student list may include identities of multiple students being screened during a mass vision screening event. For instance, the student list may include an identity of the student 102. In some implementations, the student list consolidator 108 may generate the student codes for the multiple students in the student list. For instance, each student may be associated with a unique student code. In some cases, the student list consolidator may store a table associating the student codes with identities of the multiple students. The student list consolidator 108 may further generate barcodes based on the student codes. For instance, each student code may be associated with a unique barcode. In various instances, the student list consolidator 108 may further generate an image of the multiple barcodes. The image may be output to a printer 126.

The printer 126 may be configured to print ink onto a substrate. In various cases, the printer 126 may be configured to print the image of the multiple barcodes onto a sticker substrate. Each barcode may be printed onto a separable sticker in the sticker substrate. The sticker 104 may be one of the stickers printed onto the sticker substrate by the printer 126. Once the stickers are printed, individual stickers can be affixed to the multiple students being screened. Accordingly, the student list consolidator 108 may enable the multiple students to be efficiently and accurately screened during a mass vision screening event.

The environment 100 may also enable an educator 128 to access vision screening and/or eye exam results of the student 102. In various implementations, the results of the vision screening (e.g., the health indicator(s)) can be stored in a record of the student 102 in the student record database 114 of the student record system 116. The educator 128 may access the record of the student 102 via an educator device 130. The educator device 130 may be a UE configured to communicate with the student record 116 via one or more communication interfaces. The record of the student 102 may include various education-related information about the student 102, such as grades, test scores, attendance records, teachers, and the like. Because the record may further include the health indicator(s) and/or the results of an eye exam of the student 102 performed by the eye care specialist 122, the educator 128 may be able to identify whether the student 102 is suffering from eye-related difficulties. Accordingly, the educator 128 may be able to identify whether a decline in grades of the student 102, or of some other metric of classroom performance, can be attributed to vision difficulties or some other problem. For instance, if the results of the eye exam indicate that the student 102 should be wearing corrective lenses, and the student 102 is not wearing corrective lenses, the educator 128 may identify that the problem with the student's 102 classroom performance can be resolved by the student 102 wearing the corrective lenses.

Figure 2:
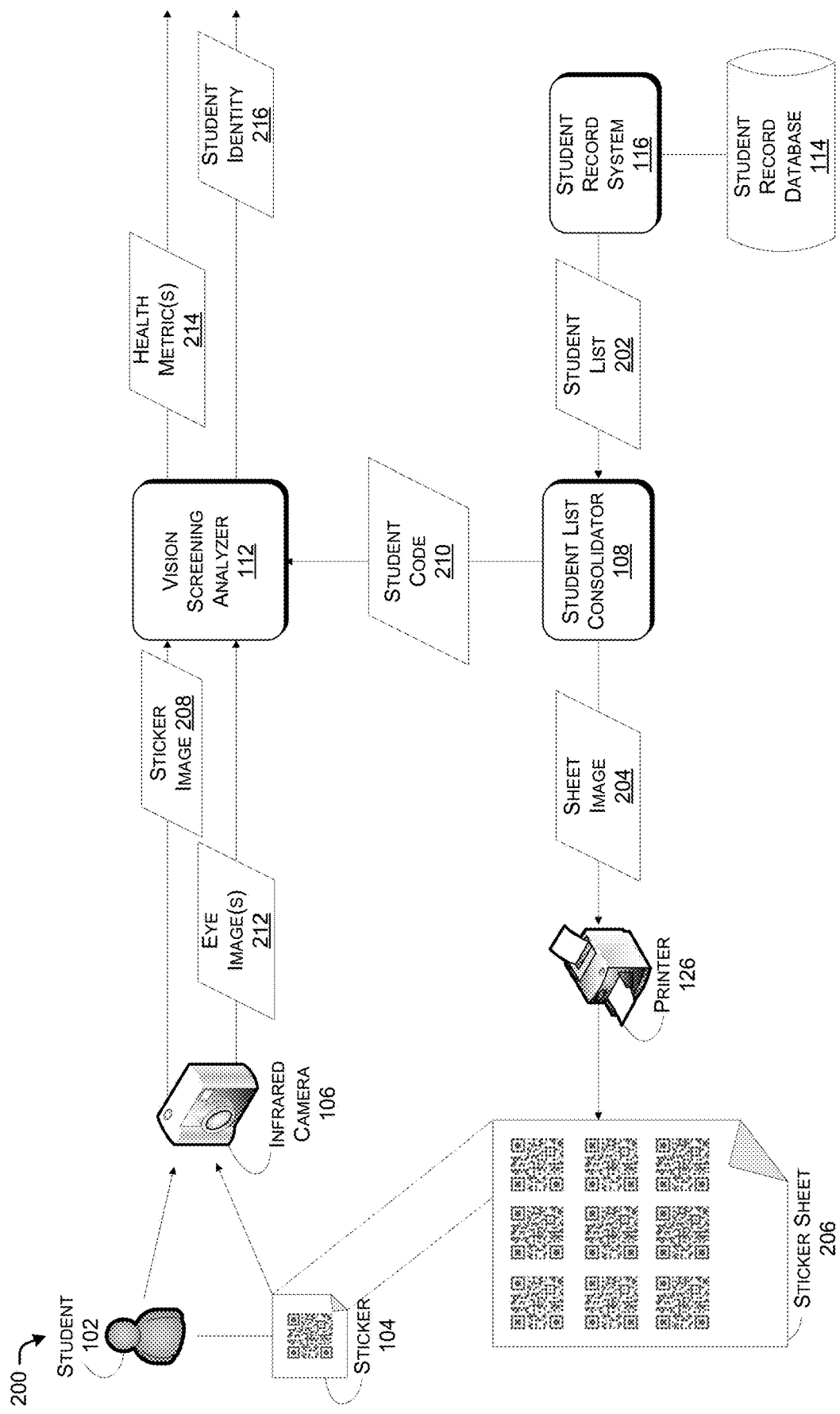
FIG. 2 illustrates an example environment for confirming the identity of an individual using a personalized barcode during a vision screening event.

FIG. 2 illustrates an example environment 200 for confirming the identity of an individual using a personalized barcode during a vision screening event. As illustrated, the environment 200 may include at least one of the student 102, the sticker 104, the infrared camera 106, the student list consolidator 108, the student record database 114, the student record system 116, and the printer 126 described with reference to FIG. 1.

In various implementations, the student record system 116 may transmit a student list 202 to the student list consolidator 108. In some cases, the student record system 116 may generate the student list based on one or more entries of a table stored in the student record database 114. The student list 202 may indicate identities of multiple students being screened in a mass vision screening event. For instance, the student list 202 could indicate the identities of 100-900 students including the student 102.

Using the student list 202, the student list consolidator 108 may generate student codes for the multiple students. For instance, each of the students may be assigned a unique student code. The student codes can identify the students directly (e.g., they may be student identification numbers), or indirectly (e.g., the student codes may be associated with the identities of the students). In some cases, the student list consolidator 108 may store a table associating the student codes with identities of the multiple students. For example, one entry in the table may include a particular student code associated with information identifying a student 102, who may be associated with the student code.

The student list consolidator 108 may generate barcodes associated with the student codes. The student list consolidator 108 may generate a unique barcode encoding each one of the student codes. For instance, the student list consolidator 108 may generate a barcode associated with the student 102 based on the unique student code associated with the student 102.

The student list consolidator 108 may further generate a sheet image 204 based on the generated barcodes. The sheet image 204 may depict the multiple barcodes in a single image. For instance, the sheet image 204 may include multiple barcodes arranged in rows and columns in a single image. The student list consolidator 108 may transmit the sheet image 204 to the printer 126. The printer 126 may print the sheet image 204 onto a sticker substrate using ink, thereby generating a sticker sheet 206. The sticker sheet 206 may include multiple separable stickers (including the sticker 104), each printed with an individual barcode among the multiple barcodes. The stickers in the sticker sheet 206 may be individually peeled and affixed to the students respectively associated with the stickers. For example, the sticker 104 may be peeled from the sticker sheet 206 and affixed to the student 102.

In various implementations, the infrared camera 106 may capture an image of the sticker 104, thereby generating the sticker image 208. The sticker image 208 may be an infrared image depicting the barcode on the sticker 104. The infrared camera 106 may transmit the sticker image 208 to the vision screening analyzer 112 for further processing.

In some cases, the vision screening analyzer 112 may analyze the sticker image 208. The vision screening analyzer 112 may extract the student code associated with the student 102 from the sticker image 208. The student list consolidator 108 may further transmit an indication of the student code 210 to the vision screening analyzer 112. The student code 210 may further include an indication of the identity of the student 102.

In various instances, the vision screening analyzer 112 may identify the student 102 by comparing the student code extracted from the sticker image 208 with the student code 210 received from the student list consolidator 108. Although not illustrated in FIG. 2, if the student code extracted from the sticker image 208 does not match the student code 210 received from the student list consolidator 108 (or an unexpected student code identified by the student list consolidator 108), the infrared camera 106 may refrain from performing the vision screening until an identity of the student 102 is confirmed via some other strategy. In some cases, the vision screening analyzer 112 may confirm the identity of the student 102 using another identification method, such as facial recognition, operator input, and/or an order of appearance of the student 102 in a group of students being screened.

The infrared camera 106 may further capture one or more eye images 212 of the student 102. In some cases, the eye image(s) 212 may depict a red reflex of one or both eyes of the student 102, an image of a reflected ring of one or both retinas of the student 102, eye tracking of the student 102 (e.g., as the student 102 reads text), or the like. The infrared camera 106 may transmit the eye image(s) 212 to the vision screening analyzer 112. Based on the eye image(s) 212, the vision screening analyzer 112 may identify one or more health metrics 214 of the student 102. The health metric(s) 214 may include at least one of a pupillary distance of the eyes of the student 102, a pupil size of each of the eyes of the student 102, a complete refraction of each of the eyes of the student 102, an alignment indicator of the eyes of the student 102, or one or more fixation and/or saccadic events indicative of a concussion and/or potential neurological condition of the student 102 (e.g., dyslexia).

In various cases, the vision screening analyzer 112 may output the health metric(s) 214 with the identity 216 of the student 102. For example, the vision screening analyzer 112 may cause an output device to display the health metric(s) and/or the identity 216 of the student 102 to an operator facilitating the vision screening process. In some cases, the vision screening analyzer 112 may store the health metric(s) 214 with the identity 216 of the student 102 in a database. In some examples, the vision screening analyzer 112 can export the health metric(s) 214 and the student identity 216 to a health record system. According to various instances, the vision screening analyzer 112 can export the health metric(s) 214 and the student identity 216 to a student record system. In some cases, the vision screening analyzer 112 may further identify whether the student 102 should have a follow-up eye exam with an eye care specialist based on the health metric(s) 214. The vision screening analyzer 112 may further cause the output device to display and/or the health record to store an indication that the student 102 should follow up with the eye care specialist.

Figure 3:
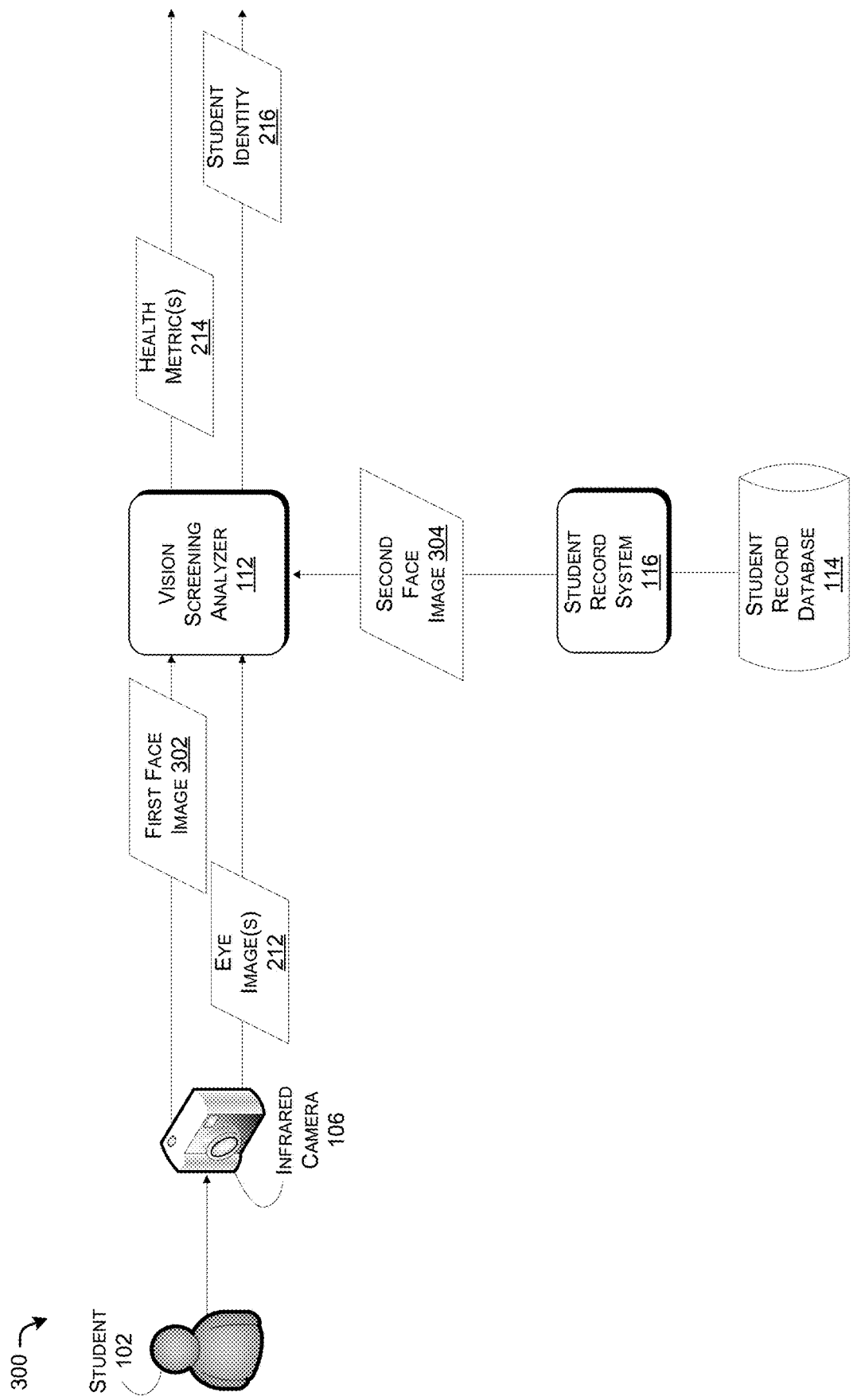
FIG. 3 illustrates an example environment for confirming the identity of an individual using facial recognition during a vision screening event.

FIG. 3 illustrates an example environment 300 for confirming the identity of an individual using facial recognition during a vision screening event. As illustrated in FIG. 3, the environment 300 may include at least one of the student 102, the infrared camera 106, the vision screening analyzer 112, the student record database 114, and the student record system 116 described above with reference to FIG. 1. The environment 300 may also include data described above with reference to FIG. 2, such as the eye image(s) 212, the health metric(s) 214, and the student identity 216.

In various implementations, the infrared camera 106 captures a first face image 302 of the student 102. In some cases, a different camera, such as a digital camera configured to capture visible light images, captures the first face image 302 of the student 102. The first face image 302 may depict the face of the student 102. The infrared camera 106 may transmit the first face image 302 to the vision screening analyzer 112 for further processing.

In addition, the student record system 116 may transmit a second face image 304 to the vision screening analyzer 112. In some cases, the student record database 114 may store the second face image 304 as part of a student profile associated with the student 102. The student profile including the second face image 304 may be accessed by the student record system 116. In some cases, additional information in the student profile can be also transmitted from the student record system 116 to the vision screening analyzer 112. For example, the student record system 116 may also transmit a message indicating the identity of the student 102 to the vision screening analyzer 112 along with the second face image 304.

The vision screening analyzer 112 may determine the identity of the student 102 by comparing the first face image 302 and the second face image 304. For instance, the vision screening analyzer 112 may perform at least one facial recognition technique on the first face image 302 and the second face image 304 to identify whether the faces depicted in the first face image 302 and the second face image 304 match. The faces may be determined to match if at least one feature depicted by the captured faces are identical or within a predetermined range of one another.

In some cases, the vision screening analyzer 112 may extract at least one feature (e.g., distances, proportions, weights, or the like) of the face depicted in each of the first face image 302 and the second face image 304, and may compare the feature(s) of the first face image 302 to the feature(s) of the second face image 304. If the features are sufficiently similar (e.g., if points, locations, coordinates, weights, or other identifiable characteristics of the second image are within a predetermined range of corresponding points, locations, coordinates, weights, or other identifiable characteristics of the third image), the vision screening analyzer 112 may determine that the same face is depicted in the first face image 302 and the second face image 304. If the features are sufficiently dissimilar (e.g., they are outside of a predetermined range of each other), the vision screening analyzer 112 may determine that different faces are depicted in the first face image 302 and the second face image 304. For example, a set of first weights between an image vector of the first face image 302 and predetermined set of Eigenfaces can be calculated. The first weights can be compared to second weights between an image vector of the second face image 304 and the predetermined set of Eigenfaces. If at least one of the first weights is within a predetermined range of the second weights (e.g., if all of the first weights are within a predetermined range of the second weights), the faces depicted in the first face image 302 and the second face image 304 may be determined to match. In various implementations, other facial recognition techniques can be used to determine whether the face depicted in the first face image 302 is or is likely to be the same face depicted in the second face image 304. If the vision screening analyzer 112 determines that the faces match, the vision screening analyzer 112 may identify the student 102. In some cases, the vision screening analyzer 112 may confirm the identity of the student 102 using another identification method, such as barcode recognition, operator input, and/or an order of appearance of the student 102 in a group of students being screened.

The infrared camera 106 may further capture one or more eye images 212 of the student 102. In some cases, the eye image(s) 212 may depict a red reflex of one or both eyes of the student 102, an image of a reflected ring of one or both retinas of the student 102, eye movements, or the like. The infrared camera 106 may transmit the eye image(s) 212 to the vision screening analyzer 112. Based on the eye image(s) 212, the vision screening analyzer 112 may identify one or more health metrics 214 of the student 102. The health metric(s) 214 may include at least one of a pupillary distance of the eyes of the student 102, a pupil size of each of the eyes of the student 102, a complete refraction of each of the eyes of the student 102, an alignment indicator of the eyes of the student 102, or one or more fixation and/or saccadic events indicative of a concussion and/or potential neurological condition of the student 102 (e.g., dyslexia).

In various cases, the vision screening analyzer 112 may output the health metric(s) 214 with the identity 216 of the student 102. For example, the vision screening analyzer 112 may cause an output device to display the health metric(s) and/or the identity 216 of the student 102 to an operator facilitating the vision screening process. In some cases, the vision screening analyzer 112 may store the health metric(s) 214 with the identity 216 of the student 102 in a database. In some examples, the vision screening analyzer 112 can export the health metric(s) 214 and the student identity 216 to a health record system. According to various instances, the vision screening analyzer 112 can export the health metric(s) 214 and the student identity 216 to a student record system. In some cases, the vision screening analyzer 112 may further identify whether the student 102 should have a follow-up eye exam with an eye care specialist based on the health metric(s) 214. The vision screening analyzer 112 may further cause the output device to display and/or the health record to store an indication that the student 102 should follow up with the eye care specialist.

Figure 4:
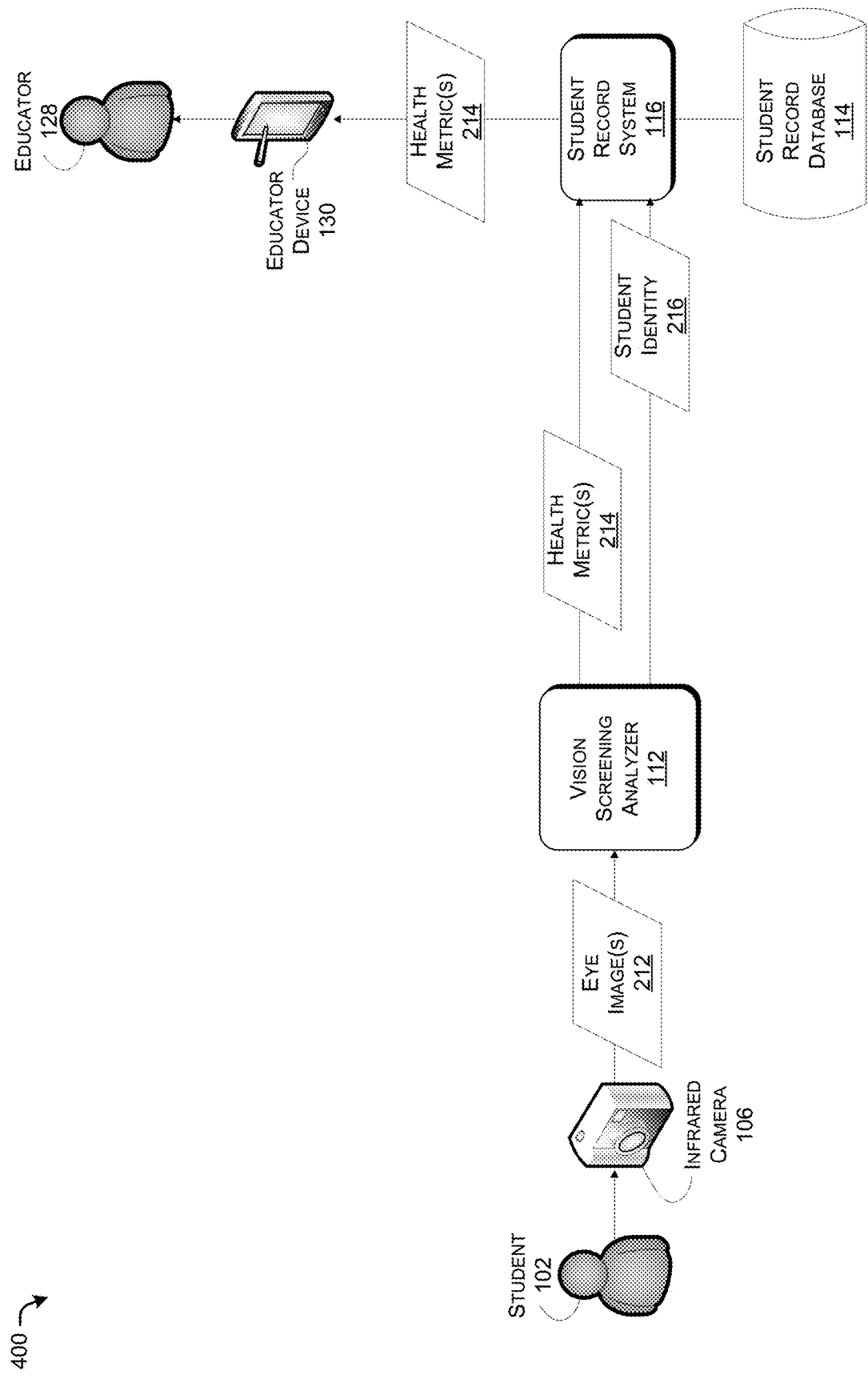
FIG. 4 illustrates an example environment for reporting vision screening results to an educator.

FIG. 4 illustrates an example environment 400 for reporting vision screening results to the educator 128. As illustrated, the environment 400 may include at least one of the student 102, the infrared camera 106, the vision screening analyzer 112, the student record database 114, the student record system 116, the educator 128, and the educator device 130 described above with reference to FIGS. 1 to 2. In addition, the environment 400 can utilize data described above with reference to FIGS. 2 and 3, such as the eye image(s) 212, the health metric(s) 214, and the student identity 216.

In various implementations, the infrared camera 106 may capture the eye image(s) 212 of the student 102. In some cases, the eye image(s) 212 may depict a red reflex of one or both eyes of the student 102, an image of a reflected ring of one or both retinas of the student 102, eye movements of the student 102, or the like. The infrared camera 106 may transmit the eye image(s) 212 to the vision screening analyzer 112. Based on the eye image(s) 212, the vision screening analyzer 112 may identify one or more health metrics 214 of the student 102. The health metric(s) 214 may include at least one of a pupillary distance of the eyes of the student 102, a pupil size of each of the eyes of the student 102, a complete refraction of each of the eyes of the student 102, an alignment indicator of the eyes of the student 102, or one or more fixation and/or saccadic events indicative of a concussion and/or potential neurological condition of the student 102 (e.g., dyslexia).

In various cases, the vision screening analyzer 112 may output the health metric(s) 214 with the identity 216 of the student 102. For example, the vision screening analyzer 112 may cause an output device to display the health metric(s) and/or the identity 216 of the student 102 to an operator facilitating the vision screening process. In some cases, the vision screening analyzer 112 may store the health metric(s) 214 with the identity 216 of the student 102 in a database. In some examples, the vision screening analyzer 112 can export the health metric(s) 214 and the student identity 216 to a health record system. In some cases, the vision screening analyzer 112 may further identify whether the student 102 should have a follow-up eye exam with an eye care specialist based on the health metric(s) 214. The vision screening analyzer 112 may further cause the output device to display and/or the health record to store an indication that the student 102 should follow up with the eye care specialist.

As illustrated in FIG. 4, the vision screening analyzer 112 may transmit the health metric(s) 214 and the student identity 216 to the student record system 116. In response to receiving the health metric(s) 214 and the student identity 216, the student record system 116 may store the health metric(s) 214 in a student profile associated with the student identity 216. For instance, the student record database 114 may store multiple student profiles associated with multiple students, wherein one of the student profiles is associated with the student 102. The student profiles may include various education-related information, such as grades, test scores, and the like.

The educator 128 may access the student profile of the student 102 via the educator device 130. In some cases, the educator 128 may further access additional student profiles of other students that the educator 128 is responsible for overseeing, teaching, or the like. For instance, the educator 128 may sign onto an educator account associated with the educator 128 hosted by a website or application output by the educator device 130. The website and/or application may display a dashboard user interface by which the educator 128 can selectively access student profiles of the students including the student 102.

When the educator 128 accesses the student profile of the student 102, the student record system 116 may transmit the health metric(s) 214 of the student 102 to the educator device 130. The educator device 130 may display or otherwise output an indication of the health metric(s) 214. The educator 128 may therefore be informed about the health metric(s) 214 via the educator device 130.

In some cases, the student profile of the student 102 may also store the results of an eye exam performed by an eye care specialist. For instance, a health record system may transmit the results of the eye exam to the student record system 116, which may store the results of the eye exam in the student profile of the student 102.

In some cases, the educator 128 may identify that a classroom performance of the student 102 appears to be deteriorating or is at a relatively low level. For instance, test scores and/or grades of the student 102 may be decreasing or may be sustained at a relatively low level. By accessing the health metric(s) 214 and/or the results of the eye exam, the educator 128 may confirm whether the poor classroom performance of the student 102 may be attributable to poor vision by the student 102. In some cases, the educator 128 may intervene by encouraging the student 102 to wear corrective lenses, or informing parents and/or guardians of whether the student 102 is wearing corrective lenses, as indicated by the health metric(s) 214.

Figure 5:
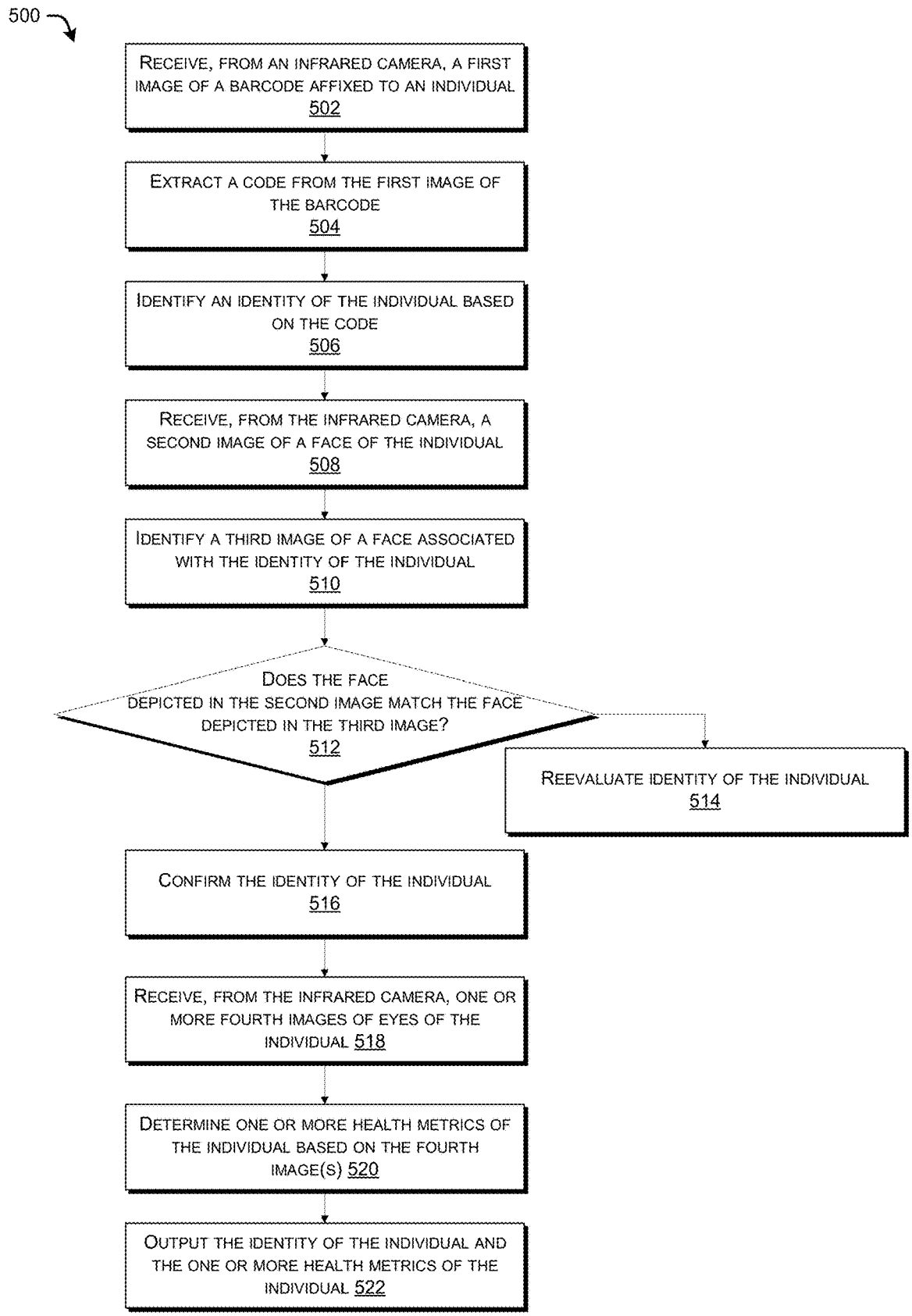
FIG. 5 illustrates an example process for performing vision screening of the individual.

FIG. 5 illustrates an example process 500 for performing vision screening of the individual. In various examples, the process may be performed by one or more processors in a vision screening analyzer, such as the vision screening analyzer 112 described above with reference to FIGS. 1 to 4.

At 502, the processor(s) may receive a first image of a barcode affixed to an individual. In some cases, the first image can be received from an infrared camera, a barcode scanner/reader, a visible light digital camera, a QR code reader, or the like. The first image may be an infrared image, visual image, or the like, in some cases. In various implementations, the barcode may be printed on a sticker that is attached to the individual. In some cases, the individual is a student, such as one of many students being screened in a mass vision screening event.

At 504, the processor(s) may extract a code from the first image of the barcode. In various implementations, the barcode can be a 1D barcode, a 2D barcode, or the like that directly encodes the code. The code may be one or more numbers, alphanumeric strings, or the like.

At 506, the processor(s) may identify an identity of the individual based on the code. In various cases, the code may be uniquely associated with the identity of the individual. For instance, the code may represent a name of the individual, a student ID number of the individual, or the like. In some cases, the code may be stored in a profile (e.g., an entry of a table) associated with the individual. For instance, the processor(s) may determine the identity of the individual by looking up the profile containing the code and extracting the identity of the individual from the entry. The identity, for example, may include at least one of a name of the individual, an age of the individual, a date of birth of the individual, a name of a teacher of the individual, an age of the individual, a gender of the individual, or an identification number of the individual. In some cases, the processor(s) may output an indicator of the identity of the individual associated with the code to a user. For example, the processor(s) may cause a display to output an image of the individual associated with the code and/or the name of the individual associated with the code to an operator, such that the operator may confirm that the individual being screened is the individual associated with the code.

At 508, the processor(s) may receive, from the infrared camera, a second image of a face of the individual. In various examples, the second image may be an infrared image, a visible light image, or the like, of the face of the individual being screened. The second image may at least depict the eyes, nose, mouth, and chin of the individual being screened.

At 510, the processor(s) may identify a third image of a face associated with the identity of the individual. In some cases, the third image may be stored in a student record and/or health record associated with the individual. For instance, upon identifying the identity of the individual based on the barcode, the processor(s) may retrieve a previously obtained image of the face of the individual stored in the student record of the individual. In some cases, the third image may be a student identification image of the individual associated with the barcode. The third image may be stored locally in a device including the processor(s). In some cases, the third image can be requested from a remote device based on the identity of the individual that was derived based on the barcode.

At 512, the processor(s) may determine whether the face depicted in the second image matches the face depicted in the third image. In various examples, the processor(s) may perform facial recognition based on the second image and the third image. For instance, the processor(s) may extract at least one feature (e.g., distances, proportions, weights, or the like) of the face depicted in each of the second image and the third image and may compare the feature(s) of the second image to the feature(s) of the third image. If the features are sufficiently similar (e.g., if points, locations, coordinates, weights, or other identifiable characteristics of the second image are within a predetermined range of corresponding points, locations, coordinates, weights, or other identifiable characteristics of the third image), the processor(s) may determine that the same face is depicted in the second image and the third image. If the features are sufficiently dissimilar (e.g., they are outside of a predetermined range of each other), the processor(s) may determine that different faces are depicted in the second image and the third image.

If the processor(s) determine that the face depicted in the second image does not match the face depicted in the third image at 512, then the process 500 proceeds to 514. At 514, the processor(s) may reevaluate identity of the individual. At 514, the processor(s) may determine that the barcode does not match the individual wearing the barcode. Accordingly, the processor(s) may use at least one other method to identify and/or confirm the identity of the individual. For instance, the processor(s) may receive, from a device associated with an operator of a vision screening device, an indication of the identity of the individual. If the indication matches the identity of the individual derived from the barcode, the processor(s) may confirm the identity of the individual. However, if the individual's identity is not confirmed, the processor(s) may output an error message or some other indicator of the unknown identity of the individual being screened. For instance, the error message may be output by the device associated with the operator.

If, however, the processor(s) determines that the face depicted in the second image matches the face depicted in the third image at 512, the process 500 may proceed to 516. At 516, the processor(s) may confirm the identity of the individual. Any subsequent vision screening analysis performed by the processor(s) may be associated with the confirmed identity of the individual.

At 518, the processor(s) may receive, from the infrared camera, one or more fourth images of eyes of the individual. In some cases, the fourth image(s) may include at least one image of a red reflex, a focused image on a retina of the individual, a video of eye movements of the individual, or the like. For instance, the infrared camera may illuminate the eyes of the individual to obtain at least one image of one or both red reflexes of the individual. In some cases, the infrared camera may transmit infrared light to the eyes of the individual at different magnification levels and the processor(s) may identify a particular magnification level at which the infrared light is focused on at least one retina of the individual.

At 520, the processor(s) may determine one or more health metrics of the individual based on the fourth image(s). In various implementations, the health metric(s) may include at least one of a pupillary distance of the eyes of the individual, a pupil size of each of the eyes of the individual, a complete refraction of each of the eyes of the individual, an alignment indicator of the eyes of the individual, or one or more fixation and/or saccadic events indicative of a concussion and/or potential neurological condition of the student 102 (e.g., dyslexia). In some cases, the processor(s) may determine whether the individual should have a follow-up eye exam with an eye care specialist based on the health metric(s). For instance, the processor(s) may determine to refer the individual if the processor(s) determine that at least one pupil size is outside of a predetermined range (e.g., 2 to 4 millimeters), at least one diopter value of a refractive test in which at least one retina is focused is outside of a particular range (e.g., −1 to +1 diopters), the eyes of the individual are out of alignment by greater than a predetermined amount (e.g., greater than 1 millimeter), dark spots are determined to be on at least one red reflex, an asymmetry between the red reflexes of the eyes, or the like. In some cases, the processor(s) may generate a message indicating that the individual should follow up with an eye care specialist.

At 522, the processor(s) may output the identity of the individual and the one or more health metrics of the individual. In some cases, the processor(s) may cause the device associated with the operator to output the identity of the individual and the health metric(s). The processor(s) may further cause the device to output the message indicating that the individual should follow up with the eye care specialist. In some implementations, the processor(s) may export the identity of the individual and the health metric(s) to a student record system and/or a health record system. The processor(s) may, in various examples, export the message indicating that the individual should follow up with the eye care specialist.

Figure 6:
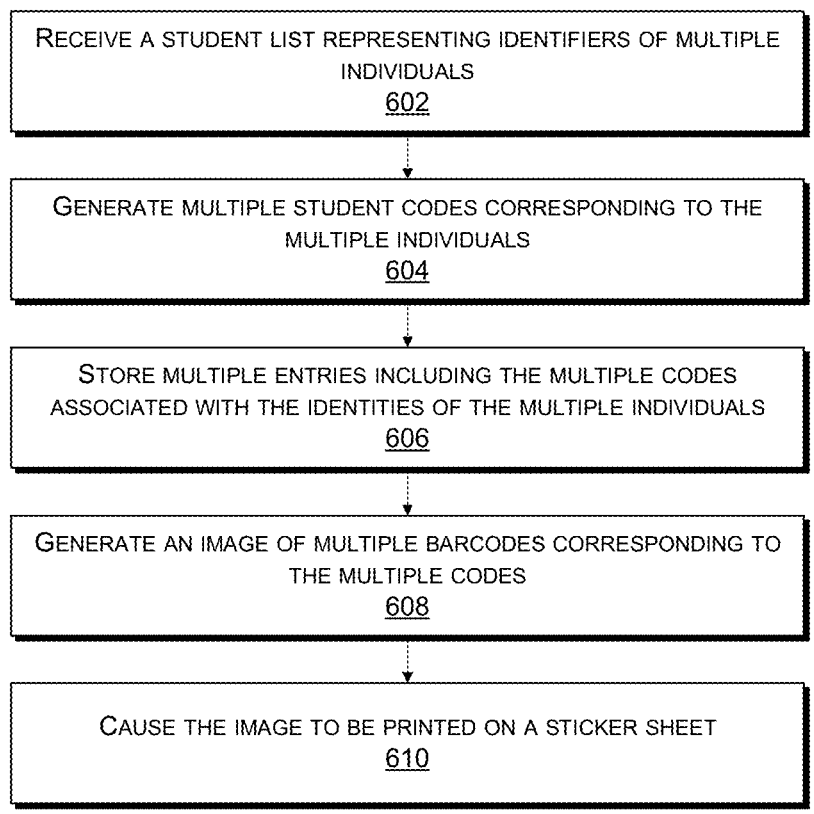
FIG. 6 illustrates an example process for automatically generating personalized stickers for students undergoing vision screening.

FIG. 6 illustrates an example process 600 for automatically generating personalized stickers for students undergoing vision screening. In various examples, the process may be performed by one or more processors in a student list consolidator, such as the student list consolidator 108 described above with reference to FIGS. 1 to 4.

At 602, the processor(s) may receive a student list representing identifiers of multiple individuals. In various examples, the student list may be a list of identities of various individuals to be screened in a mass vision screening event. For instance, the student list may be extracted from a student record system and/or student record database.

At 604, the processor(s) may generate multiple student codes corresponding to the multiple individuals. In various examples, each one of the student codes may uniquely identify one of the individuals, such that no individual is associated with the same code. In some cases, the student codes can be student ID numbers. In various examples, the student codes can be numbers, alphanumeric strings, or the like.

At 606, the processor(s) may store multiple entries including the multiple codes associated with the identities of the multiple individuals. In some cases, the multiple entries can be student profiles of the individuals. According to some implementations, the processor(s) may store the entries in a table and/or database. In various instances, the entries may be indexed by code.

At 608, the processor(s) may generate an image of multiple barcodes corresponding to the multiple codes. For instance, the processor(s) may generate 1D barcodes, 2D barcodes, or the like that directly encode the multiple codes. Accordingly, each one of the individuals may be associated with a unique barcode. The barcodes may be arranged in rows and columns in the image. The processor(s) may also generate the image to print an identity of one of the individuals adjacent to each corresponding barcode. In some cases, the image may correspond to a size of a sticker substrate to be printed.

At 610, the processor(s) may cause the image to be printed on a sticker sheet or other media. For instance, the processor(s) may transmit the image to a printer, which may print the image onto a sticker substrate using ink. In various examples, each barcode can be printed on an individual sticker. In some cases, a name or other identity corresponding to the barcode can be further printed onto each individual sticker. Accordingly, the stickers can be used to efficiently track the identities of the multiple individuals during a mass vision screening event.

Figure 7:
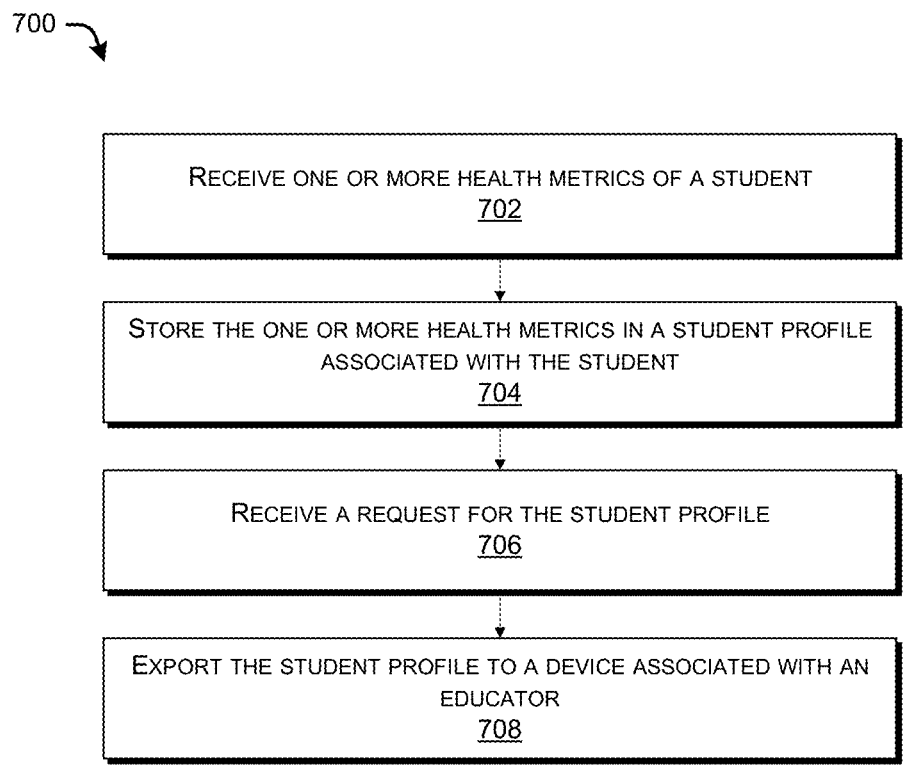
FIG. 7 illustrates an example process for reporting vision screening results of a student to an educator of the student.

FIG. 7 illustrates an example process 700 for reporting vision screening results of a student to an educator of the student. In various examples, the process may be performed by one or more processors in a student record system, such as the record system 116 described above with reference to FIGS. 1 to 4.

At 702, the processor(s) may receive one or more health metrics of a student. In various examples, the health metric(s) may include at least one eye-related health metric, which may have been obtained from a vision screening event and/or an eye exam.

At 704, the processor(s) may store (e.g., in a database) the one or more health metrics in a student profile associated with the student. The student profile may include various school-related information about the student, such as at least one of attendance records, grades, test scores, teacher names, class lists, or the like. The processors(s) may store the health metric(s) along with the school-related information about the student in the student profile.

At 706, the processor(s) may receive a request for the student profile. In various examples, the request may be received from a device associated with an educator (e.g., a teacher). The educator may seek to access the student profile via the device using an application and/or website associated with the student profile. In some cases, the request may be a request for the health metric(s) in the student profile.

At 708, the processor(s) may export, or otherwise transmit, the student profile to a device associated with an educator. The student profile may include the health metric(s). Accordingly, in some cases, the educator may identify whether a classroom performance of the student is related to the health metric(s) (e.g., eye-related health metric(s)) of the student. For instance, if the health metric(s) indicate that the student should be wearing corrective lenses in class, the educator has observed the student not wearing the corrective lenses in class, and the student's classroom performance is relatively low, the educator may be able to take corrective action by encouraging the student to wear the corrective lenses and/or requesting a parent or guardian to encourage the student to wear the corrective lenses.

Figure 8:
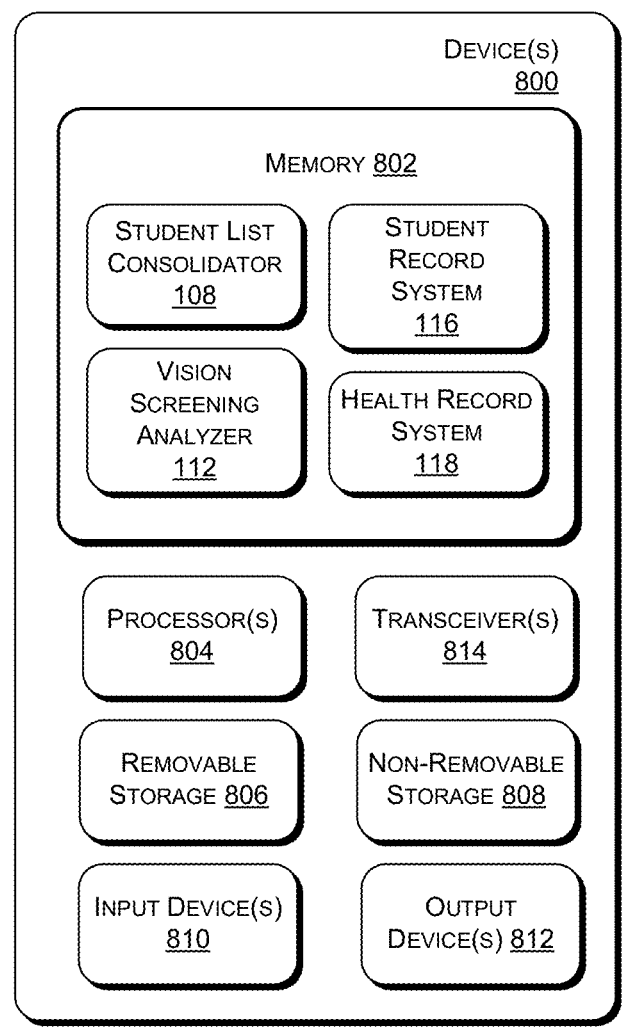
FIG. 8 illustrates example devices configured to facilitate automated vision screening of multiple individuals, such as students.

FIG. 8 illustrates example devices 800 configured to facilitate automated vision screening of multiple individuals, such as students. In some embodiments, some or all of the functionality discussed in connection with FIGS. 1-7 can be implemented in the device(s) 800. Further, the device(s) 800 can be implemented as one or more server computers, at least one network element on a dedicated hardware, as at least one software instance running on a dedicated hardware, or as at least one virtualized function instantiated on an appropriate platform, such as a cloud infrastructure, and the like. It is to be understood in the context of this disclosure that the device(s) 800 can be implemented as a single device or as a plurality of devices with components and data distributed among them.

As illustrated, the device(s) 800 can include a memory 802. The memory 802 may include various components, such as at least one of the student list consolidator 108, the vision screening analyzer 112, the student record system 116, or the health record system 118. Any of the student list consolidator 108, the vision screening analyzer 112, the student record system 116, and/or the health record system 118 can comprise methods, threads, processes, applications, or any other sort of executable instructions. Any of the student list consolidator 108, the vision screening analyzer 112, the student record system 116, or the health record system 118, and/or various other elements stored in the memory 802 can also include files and databases.

The memory 802 may include various instructions (e.g., instructions in the student list consolidator 108, the vision screening analyzer 112, the student record system 116, and/or the health record system 118), which can be executed by at least one processor 804 to perform operations. In some embodiments, the processor(s) 804 includes a Central Processing Unit (CPU), a Graphics Processing Unit (GPU), or both CPU and GPU, or other processing unit or component known in the art.

The device(s) 800 can also include additional data storage devices (removable and/or non-removable) such as, for example, magnetic disks, optical disks, or tape. Such additional storage can include removable storage 806 and non-removable storage 808. Tangible computer-readable media can include volatile and nonvolatile, removable and non-removable media implemented in any method or technology for storage of information, such as computer readable instructions, data structures, program modules, or other data. The memory 802, removable storage 806, and non-removable storage 808 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 800. Any such tangible computer-readable media can be part of the device(s) 800.

The device(s) 800 also can include input device(s) 810, such as a keypad, a cursor control, a touch-sensitive display, voice input device, etc., and output device(s) 812 such as a display, speakers, printers, etc. These devices are well known in the art and need not be discussed at length here. In particular implementations, a user can provide input to the device(s) 800 via a user interface associated with the input device(s) 810 and/or the output device(s) 812.

The device(s) 800 can also include one or more wired or wireless transceiver(s) 814. For example, the transceiver(s) 814 can include a Network Interface Card (NIC), a network adapter, a Local Area Network (LAN) adapter, or a physical, virtual, or logical address to connect to the various base stations or networks contemplated herein, for example, or the various user devices and servers. To increase throughput when exchanging wireless data, the transceiver(s) 814 can utilize Multiple-Input/Multiple-Output (MIMO) technology. The transceiver(s) 814 can include any sort of wireless transceivers capable of engaging in wireless, Radio Frequency (RF) communication. The transceiver(s) 814 can also include other wireless modems, such as a modem for engaging in Wi-Fi, WiMAX, Bluetooth, or infrared communication.

In some implementations, the transceiver(s) 814 can be used to communicate between various functions, components, modules, or the like, that are comprised in the device(s) 800. For instance, the transceiver(s) 814 can be used to transmit data between the student list consolidator 108, the vision screening analyzer 112, the student record system 116, and/or the health record system 118, between any of the student list consolidator 108, the vision screening analyzer 112, the student record system 116, or the health record system 118 and an external device or database, or the like.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

EXAMPLE CLAUSES

The following example clauses provide various implementations of the present disclosure 1. An apparatus, comprising: a camera configured to capture images; at least one processor; and memory storing instructions that, when executed by the at least one processor, cause the at least one processor to perform operations comprising: receiving, from the camera, a first image of a barcode associated with an individual; extracting an alphanumeric code from the first image of the barcode; determining an identity of the individual based on the alphanumeric code; receiving, from the camera, one or more second images of an eye of the individual; determining one or more health metrics of the individual based on the one or more second images; and storing, in an entry of a database, the identity of the individual in association with the one or more health metrics of the individual.
2. The apparatus of clause 1, wherein the first image is of a sticker worn by the individual.
3. The apparatus of clause 1 or 2, wherein determining the identity of the individual comprises: identifying, in a database, a profile associated with the alphanumeric code, the profile comprising at least one of a name of the individual, an age of the individual, a date of birth of the individual, a name of a teacher of the individual, a gender of the individual, or an identification number of the individual.

4. The apparatus of any one of clauses 1 to 3, wherein the camera is an infrared camera, the first image is an infrared image of the barcode, and the one or more second images include at least one infrared image of the eye of the individual.

5. The apparatus of any one of clauses 1 to 4, wherein the one or more health metrics comprise at least one of a pupillary distance of the individual, a pupil size of the eye of the individual, a complete refraction of the eye of the individual, an alignment indicator of the eye of the individual, or one or more fixation and/or saccadic events indicative of a concussion and/or a neurological condition.

6. The apparatus of any one of clauses 1 to 5, wherein the operations further comprise: generating a recommendation to refer the individual to an eye care specialist based on the one or more health metrics; and storing the recommendation in the entry.

7. The apparatus of any one of clauses 1 to 6, wherein the database comprises multiple entries including the entry, and each respective entry of the multiple entries corresponds to a respective individual of a plurality of individuals, the plurality of individuals including the individual, the operations further comprising: transmitting, to a remote device over at least one wireless network, the multiple entries.

8. The apparatus of any one of clauses 1 to 7, wherein the operations further comprise: receiving, from the camera, a third image of a face of the individual; receiving, from a database, a fourth image of the face of the individual; confirming the identity of the individual by comparing the third image and the fourth image; and transmitting, to the camera, a message indicating that the identity of the individual has been confirmed, wherein the camera captures the one or more second images in response to receiving the message.

9. The apparatus of any one of clauses 1 to 8, wherein the operations further comprise; transmitting, to an electronic student record system, the one or more health metrics of the individual and the identity of the individual.

10. An apparatus, comprising: a printer configured to print onto substrates; at least one processor; and memory storing instructions that, when executed by the at least one processor, cause the at least one processor to perform operations comprising: receiving, from a device, a student list representing multiple identifiers of multiple individuals; generating multiple codes respectively corresponding to the multiple individuals; storing, in a database, multiple entries comprising the multiple codes and the identifiers of the multiple individuals, wherein each of the multiple entries comprises a code among the multiple codes and an identifier among the multiple identifiers corresponding to a respective individual among the multiple individuals; generating an image of multiple barcodes respectively corresponding to the multiple codes; and transmitting the image to the printer, wherein the printer is configured to print the multiple images onto stickers.

11. The apparatus of clause 10, wherein the operations further comprise: receiving, from a vision screener, a particular code among the multiple codes; and identifying, by accessing the database, a particular entry among the multiple entries that corresponds to the particular code; extracting, from the particular entry, a particular identifier among the multiple identifiers that corresponds to a particular individual among the multiple individuals; and transmitting, to the eye screener, the particular identifier.

12. The apparatus of clause 11, wherein the operations further comprise: receiving, from the vision screener, one or more health indicators of the particular individual; and storing the one or more health indicators in the particular entry.

13. The apparatus of clause 12, further comprising: an electronic student record system comprising an electronic student record database, wherein the operations further comprise: transmitting, to the electronic student record system, the particular identifier of the particular individual and the one or more health indicators, the electronic student record system storing the one or more health indicators in a student record in the electronic student record database.

14. The apparatus of clause 13, wherein the electronic student record system is configured to receive, from an electronic device, a request for the student record associated with the particular identifier and to transmit, to the electronic device, the student record comprising the one or more health indicators.

15. The apparatus of any one of clauses 10 to 15, wherein the multiple codes comprise Uniform Resource Locators (URLs) corresponding to websites that provide vision screening results of the multiple individuals.

16. A method, comprising: capturing a first image of an individual; confirming an identity of the individual based on the first image; in response to confirming the identity of the individual, capturing one or more second images of an eye of the individual; determining one or more health metrics of the individual based on the one or more second images, the one or more health metrics comprising at least one of a pupillary distance of the individual, a pupil size of the eye of the individual, a complete refraction of the eye of the individual, an alignment indicator of the eye of the individual, or one or more fixation and/or saccadic events indicative of a concussion and/or a neurological condition; and transmitting, to a remote device, the identity of the individual and the one or more health metrics of the individual.

17. The method of clause 16, wherein the first image depicts a barcode printed on a sticker affixed to the individual and confirming the identity of the individual comprises: extracting an alphanumeric code from the barcode; and confirming the identity of the individual based on the alphanumeric code.

18. The method of clause 16 or 17, wherein the first image depicts a face of the individual and confirming the identity of the individual comprises: receiving, from the remote device, a third image of the face of the individual; and confirming the identity of the individual by comparing the first image and the third image.

19. The method of any one of clauses 16 to 18, further comprising: determining, based on the one or more health metrics, to refer the individual to an eye care specialist based on the one or more health metrics; and outputting a message indicating that the individual should follow up with the eye care specialist.

20. The method of clause 19, further comprising: transmitting, to the remote device, the message indicating that the individual should follow up with the eye care specialist.

Although the subject matter has been described, throughout this document, in language specific to structural features and/or methodological acts, it is to be understood that the subject matter defined in the appended claims is not necessarily limited to the specific features or acts described.

What is claimed is:

1. An apparatus, comprising:
a camera configured to capture images;
at least one processor; and
memory storing instructions that, when executed by the at least one processor, cause the at least one processor to perform operations comprising:
receiving, from the camera, a first image of a barcode associated with an individual;
extracting an alphanumeric code from the first image of the barcode;
determining an identity of the individual based on the alphanumeric code;
receiving, from the camera, one or more second images of an eye of the individual;
determining one or more health metrics of the individual based on the one or more second images;
receiving, from the camera, a third image of a face of the individual;
confirming the determined identity of the individual based on the third image, wherein the camera captures the one or more second images based on confirming the identity of the individual; and
storing, in an entry of a database, the identity of the individual in association with the one or more health metrics of the individual.

2. The apparatus of claim 1, wherein the first image is of a sticker worn by the individual.

3. The apparatus of claim 1, wherein determining the identity of the individual comprises:
identifying, in a database, a profile associated with the alphanumeric code, the profile comprising at least one of a name of the individual, an age of the individual, a date of birth of the individual, a name of a teacher of the individual, a gender of the individual, or an identification number of the individual.

4. The apparatus of claim 1, wherein the camera is an infrared camera, the first image is an infrared image of the barcode, and the one or more second images include at least one infrared image of the eye of the individual.

5. The apparatus of claim 1, wherein the one or more health metrics comprise at least one of a pupillary distance of the individual, a pupil size of the eye of the individual, a complete refraction of the eye of the individual, an alignment indicator of the eye of the individual, or at least one eye movement event indicative of a concussion or a neurological condition.

6. The apparatus of claim 1, wherein the operations further comprise:
generating a recommendation to refer the individual to an eye care specialist based on the one or more health metrics; and
storing the recommendation in the entry.

7. The apparatus of claim 1, wherein the database comprises multiple entries including the entry, and each respective entry of the multiple entries corresponds to a respective individual of a plurality of individuals, the plurality of individuals including the individual, the operations further comprising:
transmitting, to a remote device over at least one wireless network, the multiple entries.

8. The apparatus of claim 1, wherein the operations further comprise:
receiving, from a database, a fourth image of the face of the individual, wherein confirming the identity of the individual comprises comparing the third image and the fourth image; and
transmitting, to the camera, a message indicating that the identity of the individual has been confirmed,
wherein the camera captures the one or more second images in response to receiving the message.

9. The apparatus of claim 1, wherein the operations further comprise;
transmitting, to an electronic student record system, the one or more health metrics of the individual and the identity of the individual.

10. An apparatus, comprising:
a printer configured to print onto substrates;
at least one processor; and
memory storing instructions that, when executed by the at least one processor, cause the at least one processor to perform operations comprising:
receiving, from a device, a student list representing multiple identifiers of multiple individuals;
generating multiple codes respectively corresponding to the multiple individuals;
storing, in a database, multiple entries comprising the multiple codes and the identifiers of the multiple individuals, wherein each of the multiple entries comprises a code among the multiple codes and an identifier among the multiple identifiers corresponding to a respective individual among the multiple individuals;
generating an image of multiple barcodes respectively corresponding to the multiple codes;
transmitting the image to the printer, wherein the printer is configured to print the multiple images onto stickers;
receiving, from a vision screener, a signal indicating a particular code of the multiple codes, the particular code being identified, by the vision screener, from an image of the multiple images printed onto the stickers;
identifying a particular entry, among the multiple entries, that corresponds to the particular code;
receiving, from the vision screener, one or more health indicators of a particular individual; and
storing the health indicator in the particular entry.

11. The apparatus of claim 10, wherein the operations further comprise:
identifying, by accessing the database, the particular entry among the multiple entries that corresponds to the particular code;
extracting, from the particular entry, a particular identifier among the multiple identifiers that corresponds to the particular individual among the multiple individuals; and
transmitting, to the vision screener, the particular identifier.

12. The apparatus of claim 11, further comprising:
an electronic student record system comprising an electronic student record database,
wherein the operations further comprise:
transmitting, to the electronic student record system, the particular identifier of the particular individual and the one or more health indicators, the electronic student record system storing the one or more health indicators in a student record in the electronic student record database.

13. The apparatus of claim 12, wherein the electronic student record system is configured to receive, from an electronic device, a request for the student record associated with the particular identifier and to transmit, to the electronic device, the student record comprising the one or more health indicators.

14. The apparatus of claim 10, wherein the multiple codes comprise Uniform Resource Locators (URLs) corresponding to websites that provide vision screening results of the multiple individuals.

15. A method, comprising:
capturing a first image of an individual;
determining an identity of the individual based on the first image;
capturing a second image of a face of the individual;
confirming the determined identity of the individual based on the second image and a stored image of the individual;
in response to confirming the identity of the individual based on the second image and the stored image, capturing one or more third images of an eye of the individual;
determining one or more health metrics of the individual based on the one or more third images, the one or more health metrics comprising at least one of a pupillary distance of the individual, a pupil size of the eye of the individual, a complete refraction of the eye of the individual, an alignment indicator of the eye of the individual, or one or more eye movement events indicative of a concussion or a neurological condition; and
transmitting, to a remote device, the identity of the individual and the one or more health metrics of the individual.

16. The method of claim 15, wherein the first image depicts a barcode printed on a sticker affixed to the individual, and the method comprises:
extracting an alphanumeric code from the barcode; and
determining the identity of the individual based on the alphanumeric code.

17. The method of claim 15, further comprising receiving the stored image from the remote device and via a network, the stored image illustrating the face of the individual.

18. The method of claim 15, further comprising:
determining, based on the one or more health metrics, to refer the individual to an eye care specialist based on the one or more health metrics; and
outputting a message indicating that the individual should follow up with the eye care specialist.

19. The method of claim 18, further comprising:
transmitting, to the remote device, the message indicating that the individual should follow up with the eye care specialist.

* * * * *